United States Patent
Swift et al.

(10) Patent No.: US 6,887,971 B2
(45) Date of Patent: May 3, 2005

(54) SYNTHESIS OF POLYSUCCINIMIDE AND COPOLY(SUCCINIMIDE-ASPARTATE) IN A SUPERCRITICAL FLUID

(75) Inventors: Graham Swift, Chapel Hill, NC (US); Kenneth Michael Doll, Peoria, IL (US); Randal Lee Shogren, Chillicothe, IL (US); Ronald Alan Holser, Manito, IL (US); Julious L. Willett, Morton, IL (US)

(73) Assignee: Folia, Inc., Birmingham, AL (US)

( * ) Notice: Subject to any disclaimer, the term of this patent is extended or adjusted under 35 U.S.C. 154(b) by 27 days.

(21) Appl. No.: 10/698,398

(22) Filed: Nov. 3, 2003

(65) Prior Publication Data

US 2004/0092705 A1 May 13, 2004

Related U.S. Application Data

(63) Continuation-in-part of application No. 10/307,349, filed on Dec. 2, 2002, now Pat. No. 6,686,440, and a continuation-in-part of application No. 10/307,387, filed on Dec. 2, 2002, now Pat. No. 6,686,441, said application No. 10/307,349, is a continuation of application No. 09/776,897, filed on Feb. 6, 2001, now Pat. No. 6,495,658, said application No. 10/307,387, is a continuation-in-part of application No. 09/776,897, filed on Feb. 6, 2001, now Pat. No. 6,495,658.

(51) Int. Cl.[7] .............................................. C08G 69/10
(52) U.S. Cl. ....................... 528/328; 424/400; 424/401; 528/315; 528/322; 528/363
(58) Field of Search ................................ 424/400, 401; 528/315, 322, 328, 363

(56) References Cited

U.S. PATENT DOCUMENTS

| | | |
|---|---|---|
| 6,414,050 B1 | 7/2002 | Howdle et al. |
| 6,444,772 B1 | 9/2002 | McGinniss et al. |
| 6,486,078 B1 | 11/2002 | Rangarajan et al. |
| 6,486,355 B1 | 11/2002 | Ferrieri |
| 6,589,355 B1 | 7/2003 | Thomas et al. |

*Primary Examiner*—Terressa Boykin
(74) *Attorney, Agent, or Firm*—Stamatios Mylonakis

(57) ABSTRACT

Disclosed are methods of synthesis of polysuccinimide and a copoly(succinimide-aspartate) using a supercritical fluid.

16 Claims, 2 Drawing Sheets

SYNTHESIS OF POLYSUCCINIMIDE AND COPOLY(SUCCINIMIDE-ASPARTATE) IN A SUPERCRITICAL FLUID

This application is a Continuation-In-Part of applications Ser. Nos. 10/307,349 now U.S. Pat. No. 6,686,440 and 10/307,387, now U.S. Pat. No. 6,686,441, both filed Dec. 2, 2002, which are a Continuation and Continuation-In-Part, respectively, of application Ser. No. 09/776,897, filed Feb. 6, 2001, now U.S. Pat. No. 6,495,658, issued Dec. 17, 2002, all three of which are incorporated herein by reference in their entirety.

BACKGROUND OF THE INVENTION

1. Field of the Invention

The present invention relates to a process for the preparation of polysuccinimide and copoly(succinimide-aspartate) dissolved or dispersed in a supercritical fluid (SCF), such as liquid $CO_2$ starting with an aminoacid such as L-aspartic acid.

2. Discussion of the Related Art

L-aspartic acid has been produced commercially since the 1980's via immobilized enzyme methods. The L-aspartic acid so produced mainly has been used as a component of the synthetic sweetener, N-aspartylphenylalanine methyl ester (ASPARTAME®).

In a typical production pathway, a solution of ammonium maleate is converted to fumarate via action of an immobilized enzyme, maleate isomerase, by continuous flow over an immobilized enzyme bed. Next, the solution of ammonium fumarate is treated with ammonia also by continuous flow of the solution over a bed of the immobilized enzyme, aspartase. A relatively concentrated solution of ammonium asparate is produced, which then is treated with an acid, for example nitric acid, to precipitate aspartic acid. After drying, the resultant product of the process is powdered or crystalline L-aspartic acid. Prior art that exemplifies this production pathway includes U.S. Pat. No. 4,560,653 to Sherwin and Blouin (1985), U.S. Pat. No. 5,541,090 to Sakano et al. (1996), and U.S. Pat. No. 5,741,681 to Kato et al. (1998).

In addition, nonenzymatic, chemical routes to D,L aspartic acid via treatment of maleic acid, fumaric acid, or their mixtures with ammonia at elevated temperature have been known for over 150 years (see Harada, K., *Polycondensation of thermal precursors of aspartic acid. Journal of Organic Chemistry* 24, 1662–1666 (1959); also, U.S. Pat. No. 5,872,285 to Mazo et al. (1999)). The above chemical routes of maleic acid and ammonia are less sterically controlled as well as less quantitative and the product is a D,L racemic mixture. Although the non-enzymatic routines are significantly less quantitative than the enzymatic syntheses of aspartic acid, possibilities of continuous processes and recycling of reactants and by-products via chemical routes are envisioned.

Polymerization and copolymerization of L-aspartic acid alone or with other comonomers is known. As reviewed in U.S. Pat. No. 5,981,691 to Sikes (1999), synthetic work with polyamino acids, beginning with the homopolymer of aspartic acid, dates to the mid 1800's and has continued to the present. Interest in polyaspartates and related molecules increased in the mid 1980's as awareness of the commercial potential of these molecules grew. Particular attention has been paid to biodegradable and environmentally compatible polyaspartates for commodity uses such as detergent additives and superabsorbent materials in disposable diapers, although numerous other uses have been contemplated, ranging from water-treatment additives for control of scale and corrosion to anti-tartar agents in toothpastes.

There have been some teachings of producing copolymers of succinimide and aspartic acid or aspartate via thermal polymerization of maleic acid plus ammonia or ammonia compounds. For example, U.S. Pat. No. 5,548,036 to Kroner et al. (1996) taught that polymerization at less than 140° C. resulted in aspartic acid residue-containing polysuccinimides. However, the reason that some aspartic acid residues persisted in the product polymers was that the temperatures of polymerization were too low to drive the reaction to completion, leading to inefficient processes.

JP 8277329 (1996) to Tomida exemplified the thermal polymerization of potassium aspartate in the presence of 5 mole % and 30 mole % phosphoric acid. The purpose of the phosphoric acid was stated, in the above patent, to serve as a catalyst so that molecules of higher molecular weight might be produced. However, the products of the reaction were of a lower molecular weight than were produced in the absence of the phosphoric acid, indicating that there was no catalytic effect. There was no mention of producing copolymers of aspartate and succinimide; rather, there was mention of producing only homopolymers of polyaspartate. In fact, addition of phosphoric acid in this fashion to form a slurry or intimate mixture with the powder of potassium aspartate, is actually counterproductive to formation of copolymers containing succinimide and aspartic acid residue units, or to formation of the condensation amide bonds of the polymers in general. That is, although the phosphoric acid may act to generate some fraction of residues as aspartic acid, it also results in the occurrence of substantial amounts of phosphate anion in the slurry of mixture. Upon drying to form the salt of the intimate mixture, such anions bind ionically with the positively charged amine groups of aspartic acid and aspartate residues, blocking them from the polymerization reaction, thus resulting in polymers of lower molecular weight in lower yield.

Earlier, U.S. Pat. No. 5,371,180 to Groth et al. (1994) had demonstrated production of copolymers of succinimide and aspartate by thermal treatment of maleic acid plus ammonium compounds in the presence of alkaline carbonates. The invention involved an alkaline, ring-opening environment of polymerization such that some of the polymeric succinimide residues would be converted to the ring-opened, aspartate form. For this reason, only alkaline carbonates were taught and there was no mention of cations functioning themselves in any way to prevent imide formation.

More recently, U.S. Pat. No. 5,936,121 to Gelosa et al. (1999) taught formation of oligomers (Mw<1000) of aspartate having chain-terminating residues of unsaturated dicarboxylic compounds such as maleic and acrylic acids. These aspartic-rich compounds were formed via thermal condensation of mixtures of sodium salts of maleic acid plus ammonium/sodium maleic salts that were dried from solutions of ammonium maleate to which NaOH had been added. They were producing compounds to sequester alkaline-earth metals. In addition, the compounds were shown to be nontoxic and biodegradable by virtue of their aspartic acid composition. Moreover, the compounds retained their biodegradability by virtue of their very low Mw, notwithstanding the presence of the chain-terminating residues, which when polymerized with themselves to sizes about the oligomeric size, resulted in non-degradable polymers.

A number of reports and patents in the area of polyaspartics (i.e., poly(aspartic acid) or polyaspartate), polysuccinimides, and their derivatives have appeared more recently. Notable among these, for example, there have been disclosures of novel superabsorbents (U.S. Pat. No. 5,955, 549 to Chang and Swift, 1999; U.S. Pat. No. 6,027,804 to Chou et al., 2000), dye-leveling agents for textiles (U.S. Pat. No. 5,902,357 to Riegels et al., 1999), and solvent-free synthesis of sulfhydryl-containing corrosion and scale inhibitors (EP 0 980 883 to Oda, 2000). There also has been teaching of dye-transfer inhibitors prepared by nucleophilic addition of amino compounds to polysuccinimide suspended in water (U.S. Pat. No. 5,639,832 to Kroner et al., 1997), which reactions are inefficient due to the marked insolubility of polysuccinimide in water.

U.S. Pat. No. 5,981,691 to Sikes et al purportedly introduced the concept of mixed amide-imide, water-soluble copolymers of aspartate and succinimide for a variety of uses. The concept therein was that a monocationic salt of aspartate when formed into a dry mixture with aspartic acid could be thermally polymerized to produce the water-soluble copoly(aspartate, succinimide). The theory was that the aspartic acid comonomer when polymerized led to succinimide residues in the product polymer and the monosodium aspartate comonomer led to aspartate residues in the product polymer. It was not recognized that merely providing the comonomers was not sufficient to obtain true copolymers and that certain other conditions were necessary to avoid obtaining primarily mixtures of polyaspartate and polysuccinimide copolymers. In U.S. Pat. No. 5,981,691, the comonomeric mixtures were formed from an aqueous slurry of aspartic acid, adjusted to specific values of pH, followed by drying. There was no teaching of use of solutions of ammonium aspartate or any other decomposable cation plus NaOH, or other forms of sodium or other cations, for generation of comonomeric compositions of aspartic acid and salts of aspartate. Thus, although some of the U.S. Pat. No. 5,981,691 examples obtain products containing some copolymer in mixture with other products, particularly homopolymers, as discussed in the Summary of the Invention below, the theory that true copolymers could be obtained merely by providing the comonomers in the manner taught in U.S. Pat. No. 5,981,691 was not fully realized.

Thus, to date, there have been no successful disclosures of water-soluble or wettable, mixed amide/imide polyamino acids such as copolymers of aspartate and succinimide, related imide-containing polyamino acids, polysuccinimide or derivatives thereof.

SUMMARY OF THE INVENTION

One aspect of the invention relates to polymerizing aspartic acid to polysuccinimide in a supercritical fluid (SCF), such as liquid $CO_2$. In another aspect of the present invention aspartic acid is polymerized in a supercritical fluid to form copoly(succinimideaspartarte).

DESCRIPTION OF THE PREFERRED EMBODIMENTS

Figure 1:
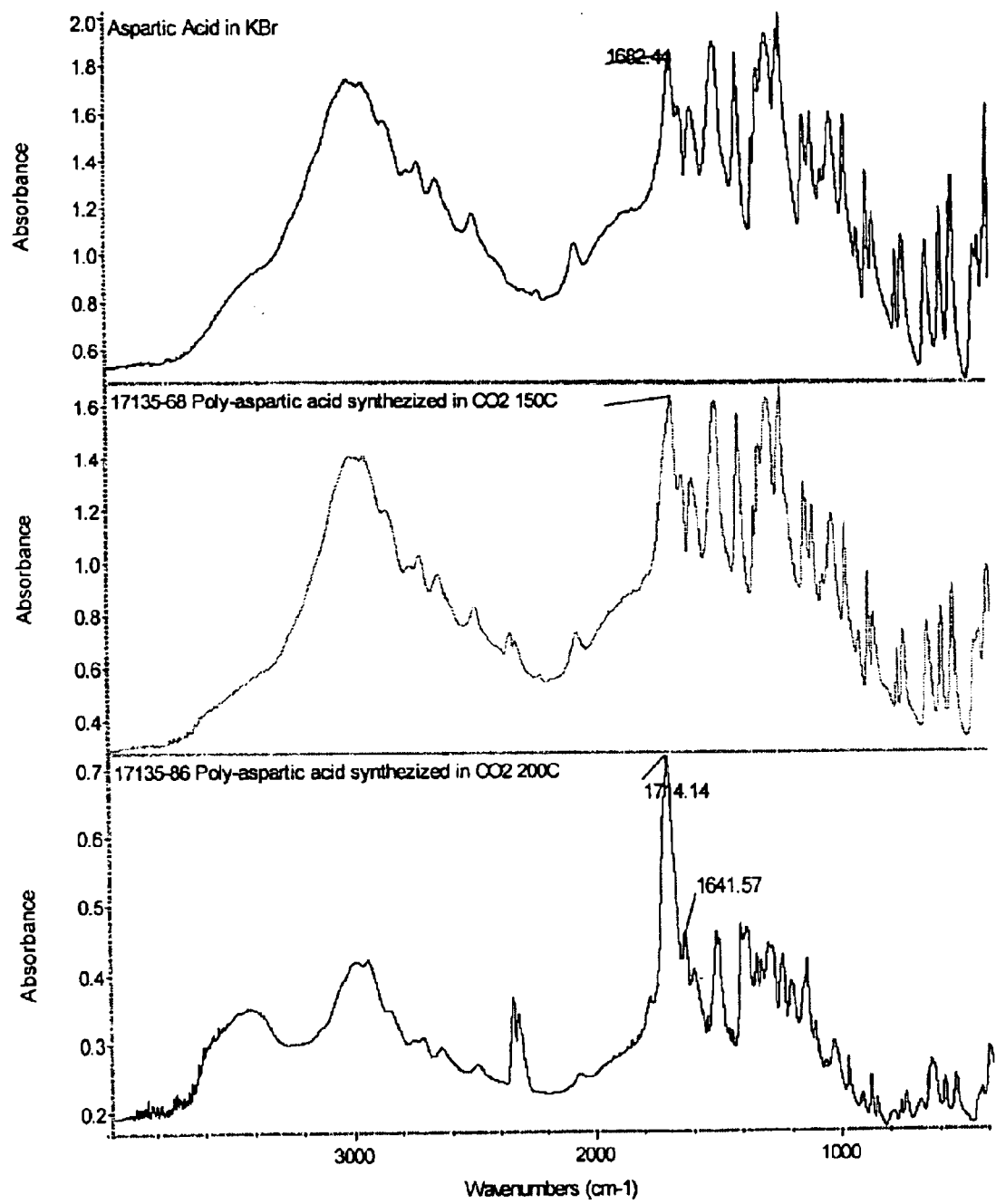
FIG. 1 depicts the IR spectra of aspartic acid and that of polysuccinimide synthesized in supercritical $CO_2$ at 150° C. (middle), and 200° C., bottom. The appearance of the imide peak at 1714 $cm^{-1}$ is only in the higher temperature synthesis.

These previous references fail to teach a method whereby a sufficiently intimate mixture of the comonomers is provided such that the polymerization leads to a true copolymer with a significant number of both aspartate and succinimide residues or the synthesis of polysuccinimide.

A. Thermal Synthesis of Copoly(succinimide-aspartate)

A method has now been discovered providing a sufficiently intimate mixture of the comonomers and, therefore, allowing the production of a true copolymer with a significant number of both aspartate (also referred to as amide) residues or units and succinimide (also referred to as imide) residues or units, as schematically shown by the following formula:

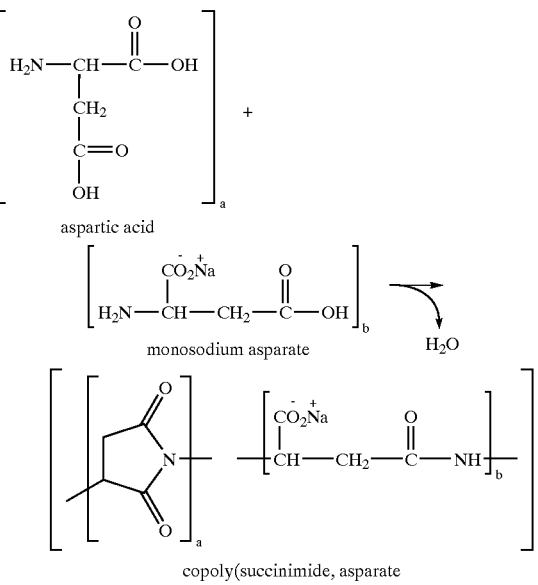

The invention also can provide the resulting copolymers in isolated form. By isolated form it is meant that the copolymer is either: (a) in the substantial absence, e.g., less than 10%, preferably less than 5%, more particularly less than 1%, by weight of a polyaspartate or polysuccinimide homopolymer, (b) prepared by a method defined by this invention or (c) polyaspartate and/or polysuccinimide homopolymer from the copolymer.

Accordingly, the present invention teaches novel methods for producing mixed amide/imide copolymers of amino acids, as well as the resulting novel imide-containing polyamino acids themselves. Included are methods employing the monomers aspartic acid or aspartate salts having non-volatile or non-heat-decomposable cations. By aspartate or aspartate salt is meant a salt of the aspartate ion and any metallic cation, including alkali metal, alkaline earth metals or transition metals. Preferably the cations are alkali or alkaline earth metals, particularly Na, Mg, K, Ca, Rb, Sr, Cs and Ba, with sodium, magnesium, potassium and calcium, particularly sodium, being preferred. These monomers lead to amide formation. Other amino acid monomers, particularly aspartates and lysine having a volatile or heat-decomposable cation, preferably an ammonium or amine cation, lead to imide formation. In the following, the amide-generating cation will be represented by sodium ($Na^+$) and the imide-generating cation will be represented by ammonium ($NH_4^+$) but with the understanding that other cations creating the same effects for achieving the invention may be substituted. By volatile or heat-decomposable cation it is meant that the cation sufficiently dissociates from the aspartate anion under the given drying conditions such that the remaining aspartate unit can cyclize to a succinimide unit during the polymerization. Cations which have at least 50% dissociation in this manner under the given drying conditions are considered volatile or heat-decomposable and cations which do not dissociate at least 50% are considered non-volatile or non-heat decomposable.

In the present invention, some elements of the conventional, enzymatic processes for production of L-aspartic acid can be adapted for producing monomers useful in the invention. The production of the comonomer mixture, however, is a novel aspect. The method involves providing an intimate solution of an aspartate of a nonvolatile cation and an aspartate of a volatile cation. By the term aspartate is meant an aspartic acid residue, either as a monomer or as a polymerized or copolymerized unit having its carboxyl group in ionic form associated with a cation, i.e., as —COO$^{31}$. Specifically, for example, an ammonium aspartate solution can be titrated with NaOH to a fractional molar equivalence of a sodium salt of aspartate and an ammonium salt of aspartate. This comonomeric solution is then dried to produce a comonomer mixture of a partial sodium salt of aspartic acid and free aspartic acid. By free aspartic acid is meant aspartic acid or a polymerized or copolymerized aspartic acid residue having its carboxyl group not in ionic form, i.e., —COOH. Because the dried comonomer mixture is prepared from the novel intimate solution of comonomers, an intimate dried mixture of these comonomers is obtained. Although not intending to be bound by this theory, it is believed that the mixture is intimate to the extent of exhibiting a salt lattice structure of the aspartate with the aspartic acid. It is possible for the dried comonomeric composition to also contain some residual ammonium aspartate, but in very small amounts, e.g., not exceeding 5% by weight, preferably not exceeding 2% by weight.

In effect, the aspartate of the volatile cation (e.g. ammonium) when dried from aqueous solution, is largely converted to powdered or crystalline aspartic acid. This is due to the loss of the decomposable cation, e.g., ammonia, as a vapor upon drying, with accompanying lowering of the pH of the evaporating solution as ammonia leaves the solution, for example, as a result of the following equilibrium being pulled to the left:

$$\uparrow NH_3 \leftrightarrows NH_3 + H_2O \leftrightarrows NH_4OH \leftrightarrows NH_4^+ + OH^-$$

As is understood, however, by those skilled in the art, the term "dried" does not imply the complete absence of ammonia. Rather, the comonomer mixture might contain an amount of ammonia which is subsequently removed during the polymerization, as described below.

The sodium ion, on the other hand, has no significant vapor phase during drying and remains in the dried salt as a counter ion to aspartate monomers. Thus, the relative proportions of the comonomers, monosodium aspartate and aspartic acid, is set by the relative molar amounts of ammonium aspartate in solution and the NaOH added to the solution prior to drying.

The dried comonomer mixture is a clear, glassy solid at ambient temperatures if drying occurs in vacuo or in an oxygen-depleted atmosphere. In the presence of atmospheric oxygen, the dried comonomer preparation has a pale yellow, glassy appearance. At reaction temperatures it is a flowable viscous liquid.

The comonomer composition of the present invention may also be prepared via nonenzymatic, chemical production of solutions of ammonium aspartate. For example, maleic acid plus ammonia in water plus heating, preferably at an elevated pressure, may produce ammonium aspartate in solution. Typically, temperatures of 80 to 160° C., preferably 120 to 160° C. and a pressure of up to about 120 psi can be used, although other conditions may be useful depending on the particular circumstances. Upon addition of the desired amount of NaOH, this solution is dried to form the comonomer composition containing the mixture of the sodium aspartate salt and aspartic acid. Drying may be effected by any of the well known procedures, for example wipe film evaporators, drum driers, and rotary evaporators.

The comonomeric composition may also be obtained via coprecipitation from solution. For example, addition of a hydrophobe or downward adjustment of pH may lead to coprecipitation of the monomers. These may then be isolated, for example by filtration, for use in the production of the imide-containing polymers.

Also included are methods in which maleic acid plus ammonia plus soluble, nonalkali as well as alkali, cationic salts are used to internally generate a combination of aspartic acid and monosodium aspartate comonomers for thermal polymerization to produce water-soluble, imide containing copolymers.

B. Synthesis of Polysuccinimide (PSI) in a Supercritical Fluid

In another embodiment of the present invention a method has now been discovered allowing the production of polysuccinimide at high molecular weight and high yield in a supercritical fluid as a solvent. A supercritical fluid is a fluid medium that is at a temperature that is sufficiently high that it cannot be liquified by pressure. A supercritical fluid relates to dense gas solutions with enhanced solvation powers, and can include near supercritical fluids. The basis for a supercritical fluid is that at a critical temperature and pressure, the liquid and gas phases of a single substance can co-exist.

Further, supercritical fluids are unique states of matter existing above certain temperatures and pressures. As such, these fluids exhibit a high level of functionality and controllability that can influence not only the macrophysical properties of the fluid, but also influence nano-structures of molecules dissolved in them.

The supercritical fluid phenomenon is documented, for example, in the *CRC Handbook of Chemistry and Physics*, 67th Edition, pages F-62 to F-64 (1986–1987), published by the CRC Press, Inc., Boca Raton, Fla. At high pressures above the critical point, the resulting supercritical fluid, or "dense gas", attains densities approaching those of a liquid and assumes some of the properties of a liquid. These properties are dependent upon the fluid composition, temperature, and pressure. As used herein, the term "critical point" denotes the transition point at which the liquid and gaseous states of a substance merge with each other and represents the combination of the critical temperature and critical pressure for a given substance.

The compressibility of supercritical fluids is great just above the critical temperature where small changes in pressure result in large changes in the density of the supercritical fluid. The "liquid-like" behavior of a supercritical fluid at higher pressures results in greatly enhanced solubilizing capabilities compared to those of the "subcritical" compound, with higher diffusion coefficients and an extended useful temperature range compared to liquids. It has also been observed that as the pressure increases in a supercritical fluid, the solubility of the solute often increases by many orders of magnitude with only a small pressure increase.

Near-supercritical liquids also demonstrate solubility characteristics and other pertinent properties similar to those of supercritical fluids. Fluid "modifiers" can often alter supercritical fluid properties significantly, even in relatively low concentrations. In one embodiment, a fluid modifier is added to the supercritical fluid. These variations are considered to be within the concept of a supercritical fluid as used in the context of this invention. Therefore, as used herein, the phrase "supercritical fluid" also denotes a compound above, at, or slightly below the critical temperature and pressure (the critical point) of that compound.

The use of supercritical fluids in the production of polymers as a swelling, foaming or purification agent is known from various sources. Supercritical fluid serves to increase resin mobility thereby improving mixing and processing, to reduce the polymer glass transition temperature by swelling, and enabling processing at lower temperatures, and acts as a solvent for impurities (including unreacted monomer and residual conventional solvents) which may be removed during the processing to give high purity products. Moreover the fluid can be used to aerate the polymer by transition to non critical gaseous state whereby a porous material may be obtained. Supercritical fluid has found application in incorporation of dyes and other inorganic materials which are insoluble in the supercritical fluid, for example inorganic carbonates and oxides, into polymers with a good dispersion to improve quality, in particular dispersion in products such as paints for spray coating and the like.

Examples of compounds which are known to have utility as supercritical fluids are, but are not limited to, $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, $CS_2$ and a mixture thereof.

Due to the low cost, environmental acceptability, non-flammability, and low critical temperature of carbon dioxide, nitrous oxide, and water, supercritical carbon dioxide, nitrous oxide and/or $H_2O$ fluid is preferably employed in the present invention. More preferably carbon dioxide is employed in the present invention.

The supercritical fluid is preferably maintained at a pressure from about 500 psi to about 2500 psi, more preferably from about 700 psi to about 2000 psi, and at a temperature from about 50° C. to about 300° C., more preferably from about 100° C. to about 250° C. The term "about" is used in the present application to denote a variation of 10% of the stated value.

The weight percentage of cosolvent and solute in the supercritical fluid is preferably from about 1% to about 20%, more preferably from about 5% to about 15%.

The weight average molecular weight of the polysuccinimide in accordance with the above process is in the order of from about 2,000 to about 10,000 Dalton, including all increments within that range, and preferably in the order of from about 3,000 to about 5,000 Daltons.

In an additional embodiment of the present invention, the polymerization of aspartic acid is performed in the dispersed phase. The term "dispersed phase" is herein used to denote a heterogeneous mixture where the monomer particles are suspended in the polymerization medium, where the polymerization medium forms the continuous phase.

C. Synthesis of Copoly(succinimide-aspartate) in a Supercritical Fluid

In another embodiment of the present invention a copoly (succinimide-aspartate) is synthesized in a supercritical fluid at high molecular weight and high yield. In accordance with this embodiment, a mixture of sodium aspartate and ammonium aspartate is prepared in a similar manner to that discussed in the thermal synthesis of copoly(succinimide-aspartate) above. This mixture is then subjected to polymerization in a supercritical fluid in a method similar to that described for the synthesis of polysuccinimide above. The weight average molecular weight is in the order of about 1,000 to about 100,000 Dalton, including all increments within that range, and preferably in the order of from 3,000 to 10,000 Daltons.

Additional comonomers may be added prior to the drying of the comonomer solution step to provide comonomeric feedstock for terpolymers and high polymers of thermally condensed polyamino acids. In particular, the amino acids lysine and glutamate and salts thereof may be used. These can impart further water-solubility to the product imide-containing polymers. Moreover, other difunctional and multifunctional monomers such as aminocaproic acid and ornithine, as well as the other common amino acids including but not limited to alanine, glycine, leucine, isoleucine, methionine which can form a sulfoxide by oxidation of the thioether, and theronine; sugar-acids such as glucuronic acid; other hydroxyl-containing carboxylates such as citric acid and malonic acids; and other like molecules, are additional comonomers that would co-condense in the production of the imide-containing polyamino acids and may be useful to provide aqueous solubility and other useful properties to the imide-containing polyamino acids.

Additional preferred comonomers include, but are not limited to caprolactan; caprolactone; glutamine; arginine; asparagine, which is inherently present in the product, in accordance with the present invention, in an amount of from 0 to 15%; and cystine, which preferably forms a disulfide which can be further subjected to reductive cleavage to yield two mercaptans, which mercaptans are available for further derivatization or oxidative cleavage to form a sulfonate. Further, additional comonomers include, but are not limited, an aminosugar, glutamine, and chitin, chitosan, at a weight average molecular weight ranging from an oligomer to 1,000,000 including all increments within the above range. Further comonomers include but are not limited to, a polysaccharide ranging in weight average molecular weight from that of an oligomer to that of a naturally occurring polysaccharide, including all increments within the above range. The term "oligomer" as used in the present application denotes a resin with a degree of polymerization (DP) between 10 and 1000.

EXAMPLES

Example 1

Procedure for Synthesis of Poly(Succinimide-aspartate) Copolymer in Supercritical $CO_2$.

The reactor employed in this reaction was a 450 mL Parr Series 4560 Bench Top Mini Stirred Reactor, equipped with a standard impeller stirrer. A mixture of sodium aspartate and ammonium aspartate was prepared in a similar manner to that done in the thermal synthesis of poly(succinimide-aspartate) copolymer disclosed in the parent application Ser. Nos. 10/307,349 and 09/776,897 now U.S. Pat. No. : 6,495,658. First, 13.3 g (0.1 mol) 1-aspartic acid was stirred with 5.1 mL 9.83 M NaOH solution (0.05 mol NaOH) and 3.25 mL of concentrated 15.43 M $NH_4OH$ (0.05 mol $NH_4OH$) in 100 mL of Nanopure $H_2O$. This mixture was stirred for 15 min and dried in a forced air oven at 80° C. for 14 hrs. After drying, the mixture was a solid with a moisture content of 3.5%. A portion of this solid (5.35 g) was ground with a mortar and pestle and added to a reactor liner. The reactor liner containing the solid was placed in the reactor and flushed with nitrogen for 1 min, then pressurized with nitrogen to 100 psi in order to test for leaks in the system. The nitrogen was vented to 10 psi. The reactor was pressurized to 787 psi from a $CO_2$ tank equipped with a syphon tube. The reactor cooling water was started, and the temperature set to 50° C. The pressure was vented to 1106 psi at 50° C., which gives a $CO_2$ density of 0.2 g/mL. The reactor temperature was set to 150° C., the stirring set to 400 RPM. The reaction was run for 4 hrs. The pressure was slowly vented to 10 psi, the reactor pressurized with nitrogen to 70 psi, and it was cooled overnight. A solid, light brown material was isolated and ground into a fine powder with a mortar and pestle (2.8 g; 68% yield after grinding). Titration by first acidifying with HCl, then titrating with NaOH showed 0.45 equivalents of carboxylate per 100 g of polymer, similar to the expected 0.43 demonstrated for poly(succinimide-aspartate) copolymer.

Example 2
Procedure for Synthesis of Polysuccinimide in Supercritical $CO_2$.

Figure 2:
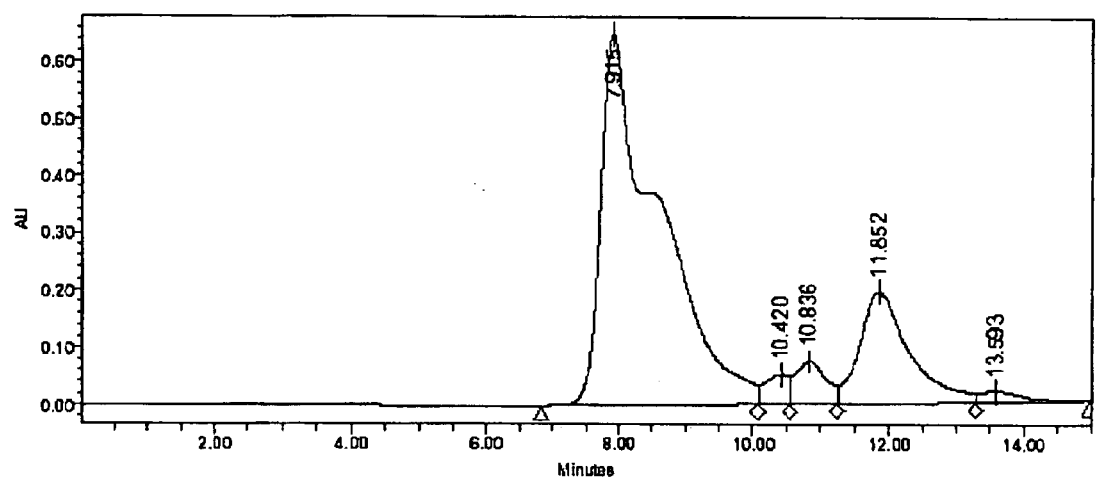
FIG. 2 is a GPC analysis of polysuccinimde synthesized in supercritical $CO_2$. The peak at 7.918 min corresponds to a MW of ~4200 Daltons when compared to sodium polyacrylate standards.

The reactor employed in this reaction was a 450 mL Parr Series 4560 Bench Top Mini Stirred Reactor, equipped with a standard impeller stirrer. First, 1.58 g (0.01 mol) 1-aspartic acid was added to the reactor liner which was placed in the reactor and flushed with nitrogen for 1 min, then pressurized with nitrogen to 100 psi in order to test for leaks in the system. The nitrogen was vented to 10 psi. The reactor was pressurized to 780 psi from a $CO_2$ tank equipped with a syphon tube. The reactor cooling water was started, and the temperature set to 70° C. The pressure was vented to 1106 psi at 70° C., which gives a $CO_2$ density of 0.16 g/mL. This lower density, compared to the poly(succinimide-aspartate) copolymer synthesis, is used so the pressure limit of the reactor will not be exceeded at the higher temperatures required for this reaction. The reactor temperature was set to 205° C., the stirring set to 400 RPM. The reaction was run for 4 hrs. The pressure was slowly vented to 10 psi, the reactor pressurized with nitrogen to 116 psi, and cooled overnight. A solid, light red product was isolated and ground with a mortar and pestle (1.07 g; 78% yield after grinding). The product was characterized by IR and GPC anlaysis. The IR (FIG. 2) shows the typical expected imide peak at 1714 $cm^{-1}$. GPC analysis (FIG. 3) show that the primary product is of a MW of ~4200 Daltons.

Obviously, numerous modifications and variations of the present invention are possible in light of the above teachings. It is therefore to be understood that within the scope of the appended claims, the invention may be practiced otherwise than as specifically described herein.

What is claimed is:

1. A method for preparing a polysuccinimide, which comprises, subjecting aspartic acid to polymerization in a solvent of supercritical fluid to form a polysuccinimide; wherein said supercritical fluid is selected from the group consisting of $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, $CS_2$ and a mixture thereof.

2. The method of claim 1, wherein said supercritical fluid is maintained at a pressure of from about 500 psi to about 2500 psi.

3. The method of claim 1, wherein said supercritical fluid is maintained at a pressure of from about 700 psi to about 2000 psi.

4. The method of claim 1, wherein said supercritical fluid is maintained at a temperature of from about 50° C. to about 300° C.

5. The method of claim 1, wherein said supercritical fluid is maintained at a temperature of from about 100° C. to about 250° C.

6. The method of claim 1, wherein the weight average molecular weight of the polysuccinimide is in the order of from about 2,000 to about 10,000 Dalton.

7. The method of claim 1, wherein the weight average molecular weight of the polysuccinimide is in the order of from about 3,000 to about 5,000 Daltons.

8. A method for preparing a copolymer containing copolymerized aspartate units and succinimide units which comprises, subjecting a comonomer mixture of aspartic acid and a salt of aspartic acid to polymerization in a solvent of a supercritical fluid.

9. The method of claim 8, wherein said comonomer mixture was prepared by drying a solution of a salt of aspartic acid having a cation which does not volatilize during the drying and a salt of aspartic acid having a cation which at least partially volatilizes to free aspartic acid during the drying.

10. The method of claim 8, wherein said supercritical fluid is selected from the group consisting of $CO_2$, $NH_3$, $H_2O$, $N_2O$, xenon, krypton, methane, ethane, ethylene, propane, pentane, methanol, ethanol, isopropanol, isobutanol, $CClF_3$, $CFH_3$, cyclohexanol, and $CS_2$ and a mixture thereof.

11. The method of claim 8, wherein said supercritical fluid is maintained at a pressure of from about 500 psi to about 2500 psi.

12. The method of claim 8, wherein said supercritical fluid is maintained at a pressure of from about 700 psi to about 2000 psi.

13. The method of claim 8, wherein said supercritical fluid is maintained at a temperature of from about 50° C. to about 250° C.

14. The method of claim 8, wherein said supercritical fluid is maintained at a temperature of from about 100° C. to about 250° C.

15. The method of claim 8, wherein the weight average molecular weight of said copolymer is in the order of about 2,000 to about 10,000 Dalton.

16. The method of claim 8, wherein the weight average molecular weight of said copolymer is in the order of from about 3,000 to about 5,000 Daltons.

* * * * *

UNITED STATES PATENT AND TRADEMARK OFFICE
CERTIFICATE OF CORRECTION

PATENT NO. : 6,887,971 B2
DATED : May 3, 2005
INVENTOR(S) : Swift et al.

It is certified that error appears in the above-identified patent and that said Letters Patent is hereby corrected as shown below:

Column 3,
Line 52, "copoly(succinimideaspartate)" should read -- copoly(succinimide-aspartate) --.

Column 5,
Line 16, "as —COO$^{31}$" should read as -- —COO$^-$ --.

Column 8,
Line 26, "caprolactan" should read -- caprolactam --.

Signed and Sealed this

Sixth Day of September, 2005

JON W. DUDAS
*Director of the United States Patent and Trademark Office*